(12) United States Patent
Maschino et al.

(10) Patent No.: US 10,258,517 B1
(45) Date of Patent: Apr. 16, 2019

(54) FLUID DISTRIBUTION MATERIAL FOR ABSORBENT ARTICLES

(71) Applicant: TREDEGAR FILM PRODUCTS CORPORATION, Richmond, VA (US)

(72) Inventors: Andrew D. Maschino, Paris, IL (US); Michael Estel Fisher, Rosedale, IN (US); Brian C. Loomis, Terre Haute, IN (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 0 days.

(21) Appl. No.: 15/989,852

(22) Filed: May 25, 2018

(51) Int. Cl.
*A61F 13/537* (2006.01)
*A61F 13/511* (2006.01)
(Continued)

(52) U.S. Cl.
CPC ...... *A61F 13/537* (2013.01); *A61F 13/15203* (2013.01); *A61F 13/513* (2013.01); *A61F 13/5376* (2013.01); *A61F 13/53708* (2013.01); *A61F 13/53713* (2013.01); *A61F 13/53747* (2013.01); *B32B 3/266* (2013.01); *B32B 3/28* (2013.01); *B32B 3/30* (2013.01); *B32B 5/022* (2013.01); *B32B 27/12* (2013.01); *A61F 13/15699* (2013.01); *A61F 13/512* (2013.01); *A61F 13/515* (2013.01); *A61F 13/5116* (2013.01); *A61F 13/51104* (2013.01); *A61F 2013/15292* (2013.01); *A61F 2013/15406* (2013.01); *A61F 2013/51165* (2013.01); *A61F 2013/51195* (2013.01); *A61F 2013/51355* (2013.01); *A61F 2013/51366* (2013.01);
(Continued)

(58) Field of Classification Search
None
See application file for complete search history.

(56) References Cited

U.S. PATENT DOCUMENTS 3,929,135 A * 12/1975 Thompson ............ A61F 13/512
604/385.08
4,324,246 A * 4/1982 Mullane ................ A61F 13/512
604/366
(Continued)

FOREIGN PATENT DOCUMENTS

DE       4016348 A1 * 11/1991  ............ B32B 37/10
DE       4016348 A1    11/1991
(Continued)

*Primary Examiner* — Jeffrey A Vonch
(74) *Attorney, Agent, or Firm* — Karceski IP Law, PLLC

(57) ABSTRACT

A fluid distribution material for use in an absorbent article includes a formed film layer having first and second sides and a basis weight of between about 10 gsm and about 25 gsm, and a nonwoven layer having a basis weight of between about 10 gsm and about 15 gsm and laminated to the formed film layer. The formed film layer includes a plurality of apertured protuberances arranged in a pattern having 10 to 40 protuberances per linear inch. Each of the protuberances includes a continuous sidewall extending from the first side, and the second side has a plurality of apertures aligned with the plurality of protuberances, and land areas in between the apertures. The nonwoven layer includes a plurality of fibers attached to the formed film layer at the land areas. The material has a rewet value of less than 0.075 grams in accordance with the Rewet Test Method.

18 Claims, 17 Drawing Sheets

(51) Int. Cl.
  *A61F 13/512* (2006.01)
  *A61F 13/515* (2006.01)
  *B32B 3/24* (2006.01)
  *B32B 3/28* (2006.01)
  *B32B 3/30* (2006.01)
  *B32B 5/02* (2006.01)
  *B32B 27/12* (2006.01)
  *B32B 27/18* (2006.01)
  *B32B 27/32* (2006.01)
  *B32B 3/26* (2006.01)
  *A61F 13/15* (2006.01)
  *A61F 13/513* (2006.01)
  *B32B 5/26* (2006.01)
  *A61F 13/53* (2006.01)

(52) U.S. Cl.
  CPC ............ *A61F 2013/51372* (2013.01); *A61F 2013/53721* (2013.01); *A61F 2013/53778* (2013.01); *A61F 2013/53782* (2013.01); *A61F 2013/53795* (2013.01); *A61F 2013/530868* (2013.01); *A61F 2013/530875* (2013.01); *A61F 2013/530897* (2013.01); *A61F 2013/530905* (2013.01); *B32B 5/26* (2013.01); *B32B 27/18* (2013.01); *B32B 27/32* (2013.01); *B32B 2307/50* (2013.01); *B32B 2307/718* (2013.01); *B32B 2307/726* (2013.01); *B32B 2307/728* (2013.01); *B32B 2323/043* (2013.01); *B32B 2555/02* (2013.01); *Y10T 428/24289* (2015.01); *Y10T 428/24331* (2015.01); *Y10T 428/24636* (2015.01); *Y10T 428/266* (2015.01); *Y10T 442/674* (2015.04); *Y10T 442/678* (2015.04)

(56) References Cited

U.S. PATENT DOCUMENTS

| | | | | |
|---|---|---|---|---|
| 4,423,101 A * | 12/1983 | Willstead | A61F 13/512 | 428/138 |
| 4,690,679 A * | 9/1987 | Mattingly, III | A61F 13/515 | 604/383 |
| 4,781,710 A | 11/1988 | Megison et al. | | |
| 4,995,930 A * | 2/1991 | Merz | B26F 1/26 | 156/209 |
| 5,135,521 A * | 8/1992 | Luceri | A61F 13/512 | 428/137 |
| 5,264,268 A * | 11/1993 | Luceri | A61F 13/5611 | 428/138 |
| 5,368,909 A | 11/1994 | Langdon et al. | | |
| 5,368,910 A | 11/1994 | Langdon | | |
| 5,383,870 A * | 1/1995 | Takai | A61F 13/512 | 604/358 |
| 5,439,458 A * | 8/1995 | Noel | A61F 13/15203 | 604/358 |
| 5,500,270 A * | 3/1996 | Langdon | A61F 13/512 | 428/116 |
| 5,580,418 A | 12/1996 | Alikham | | |
| 5,591,510 A * | 1/1997 | Junker | B32B 3/266 | 428/132 |
| 5,603,707 A | 2/1997 | Trombetta et al. | | |
| H1670 H * | 7/1997 | Aziz | A61F 13/515 | 604/367 |
| 5,647,862 A * | 7/1997 | Osborn, III | A61F 13/47227 | 604/368 |
| 5,665,452 A | 9/1997 | Langdon et al. | | |
| 5,667,619 A | 9/1997 | Alikham | | |
| 5,667,625 A | 9/1997 | Alikham | | |
| 5,669,895 A | 9/1997 | Murakami et al. | | |
| 5,709,829 A * | 1/1998 | Giacometti | A61F 13/15731 | 264/156 |
| 5,762,643 A * | 6/1998 | Ray | A61F 13/15699 | 604/383 |
| 5,827,254 A | 10/1998 | Thombetta et al. | | |
| 5,897,543 A * | 4/1999 | Francis | A61F 13/512 | 604/383 |
| 6,242,074 B1 * | 6/2001 | Thomas | A61F 13/15577 | 428/137 |
| 6,455,753 B1 | 9/2002 | Glaug et al. | | |
| 6,491,928 B1 * | 12/2002 | Smith, III | A61F 13/36 | 424/401 |
| 6,509,513 B2 | 1/2003 | Glaug et al. | | |
| 6,566,578 B1 | 5/2003 | Glaug et al. | | |
| 6,849,319 B2 | 2/2005 | Cree et al. | | |
| 7,198,836 B2 | 4/2007 | Thomas | | |
| 7,378,568 B2 | 5/2008 | Thomas et al. | | |
| 8,235,957 B2 | 8/2012 | Ponomarenko et al. | | |
| 8,344,203 B2 | 1/2013 | Seyler et al. | | |
| 8,426,671 B2 | 4/2013 | Steffen et al. | | |
| 8,581,020 B2 | 11/2013 | Seyler et al. | | |
| 8,674,171 B2 | 3/2014 | Seyler | | |
| 9,554,940 B2 | 1/2017 | Seyler et al. | | |
| 9,849,602 B2 | 12/2017 | Cree | | |
| 9,937,085 B2 | 4/2018 | Bergstrom et al. | | |
| 2002/0062113 A1 * | 5/2002 | Thomas | A61F 13/53717 | 604/378 |
| 2003/0097113 A1 * | 5/2003 | Molee | A61F 13/53747 | 604/385.101 |
| 2003/0124308 A1 * | 7/2003 | Cree | A61F 13/5146 | 428/137 |
| 2003/0195487 A1 * | 10/2003 | Thomas | B32B 5/022 | 604/385.01 |
| 2004/0087927 A1 * | 5/2004 | Suzuki | A61F 13/513 | 604/378 |
| 2005/0256475 A1 * | 11/2005 | Komatsu | A61F 13/512 | 604/378 |
| 2005/0261649 A1 * | 11/2005 | Cohen | A61F 13/53747 | 604/383 |
| 2005/0267429 A1 * | 12/2005 | Cohen | A61F 13/53747 | 604/378 |
| 2006/0087053 A1 * | 4/2006 | O'Donnell | B26F 1/18 | 264/156 |
| 2006/0161123 A1 * | 7/2006 | Kudo | A61F 13/84 | 604/383 |
| 2007/0048498 A1 * | 3/2007 | Cree | A61F 13/512 | 428/137 |
| 2007/0212545 A1 * | 9/2007 | Cree | A61F 13/537 | 428/409 |
| 2008/0114317 A1 * | 5/2008 | Seyler | A61F 13/53713 | 604/369 |
| 2009/0299316 A1 * | 12/2009 | Seyler | A61F 13/53713 | 604/378 |
| 2010/0121298 A1 * | 5/2010 | Seyler | A61F 13/53713 | 604/378 |
| 2011/0034895 A1 | 2/2011 | Schmidt et al. | | |
| 2011/0183109 A1 * | 7/2011 | Seyler | A61F 13/53743 | 428/132 |
| 2011/0184370 A1 * | 7/2011 | Seyler | A61F 13/53713 | 604/385.101 |
| 2012/0310197 A1 * | 12/2012 | Thomas | A61F 13/53713 | 604/378 |
| 2014/0128828 A1 * | 5/2014 | Andersson | A61F 13/53717 | 604/383 |
| 2016/0106602 A1 * | 4/2016 | Seyler | A61F 13/512 | 604/372 |

FOREIGN PATENT DOCUMENTS

| | | | | |
|---|---|---|---|---|
| EP | 0749738 B1 | 11/1999 | | |
| FR | 2759389 A1 * | 8/1998 | | A61F 13/5146 |
| JP | 01249052 A * | 10/1989 | | |
| KR | 20070008855 A * | 1/2007 | | |
| WO | 9309741 | 5/1993 | | |
| WO | WO-9424354 A1 * | 10/1994 | | A61F 13/15731 |
| WO | WO-9815399 A1 * | 4/1998 | | A61F 13/15731 |
| WO | WO-2007035038 A1 * | 3/2007 | | A61F 13/53713 |

* cited by examiner

FLUID DISTRIBUTION MATERIAL FOR ABSORBENT ARTICLES

FIELD

The present invention is directed to a fluid distribution material that may be used in absorbent articles, as well as absorbent articles that include the fluid distribution material.

BACKGROUND

A variety of well-known absorbent articles are configured to absorb body fluids. Examples of such absorbent articles include, but are not limited to, feminine hygiene products, such as sanitary napkins, baby diapers, adult incontinence products, and bandages. A typical absorbent article is generally constructed with a fluid permeable user-facing topsheet, which may be a three dimensional apertured polymer film or a nonwoven web or a film/nonwoven laminate, an absorbent core and a fluid impermeable garment or outwardly-facing backsheet, which may be a solid polymer film, for example.

A potential problem associated with absorbent articles may be the perceived lack of dryness of the user-facing topsheet of the absorbent article. Generally, the drier the skin feels that is contacting topsheet, the more comfortable the absorbent article. In many instances, surface dryness of the topsheet may be correlated to fluid strikethrough efficiency. If the layer(s) beneath the topsheet are inefficient in fully pulling the fluid out of the topsheet, residual wetness can remain. Moreover, wetness may reoccur and contribute to residual wetness if the fluid is allowed to move from the layer(s) beneath the topsheet and back through the topsheet when the absorbent article is subjected to pressure, which is a typical condition when the article is being worn by a user.

One or more additional layers may be added to the absorbent article in between the topsheet and absorbent core to improve fluid acquisition out of the topsheet and/or fluid distribution across the absorbent core so that the fluid may be pulled through and out of the topsheet and into the absorbent core more quickly and/or more completely. The additional layer may be in the form of a nonwoven material, such as the liquid management layer described in U.S. Pat. No. 8,426,671 (incorporated herein by reference), or may be in the form of a three dimensional apertured film, such as the acquisition distribution layer described in U.S. Pat. No. 7,378,568 (incorporated herein by reference) or the acquisition/distribution layer described in U.S. Patent Application Publication No. 2005/0267429 (incorporated herein by reference), for example. However, such an additional layer adds cost to the final article and may also increase the thickness or bulkiness and/or stiffness of the article. Efforts to minimize the amount of material that is used in an additional layer by, for example, downgauging, particularly for a film, may be challenging because downgauging may reduce the modulus of the material and negatively impact the ability to incorporate the layer into the final absorbent article during conversion processes.

It is desirable to provide a fluid distribution material that reduces residual wetness, even after the absorbent article is subjected to pressure, and has a modulus sufficient to allow the fluid distribution material to be converted into an absorbent article.

SUMMARY

According to an aspect of the invention, there is provided a fluid distribution material for use in an absorbent article. The fluid distribution material includes a formed film layer having a first side and a second side opposite the first side. The formed film layer includes a plurality of apertured protuberances arranged in a pattern having 10 to 40 protuberances per linear inch. Each of the protuberances includes a continuous sidewall extending from the first side, and the second side has a plurality of apertures aligned with the plurality of apertured protuberances, and land areas in between the apertures. The formed film layer has a basis weight of between about 10 gsm and about 25 gsm. A nonwoven layer is laminated to the second side of the formed film layer. The nonwoven layer includes a plurality of fibers attached to the formed film layer at the land areas, and has a basis weight of between about 10 gsm and about 15 gsm. The fluid distribution material has a rewet value of less than 0.075 grams in accordance with the Rewet Test Method described herein.

In an embodiment, the fluid distribution material has a compressibility of less than 10% between pressures of 0.21 psi and 0.60 psi.

In an embodiment, the plurality of apertured protuberances are arranged in a pattern having 10 to 25 protuberances per inch.

In an embodiment, the formed film layer includes a surfactant.

In an embodiment, the nonwoven layer includes a spunbond nonwoven. In an embodiment, the spunbond nonwoven is hydrophilic.

According to an aspect of the invention, there is provided a fluid management system for use in an absorbent article. The fluid management system includes a fluid distribution material that includes a formed film layer having a first side and a second side opposite the first side. The formed film layer includes a plurality of apertured protuberances arranged in a pattern having 10 to 40 protuberances per linear inch. Each of the protuberances includes a continuous sidewall extending from the first side, and the second side has a plurality of apertures aligned with the plurality of apertured protuberances, and land areas in between the apertures. The formed film layer has a basis weight of between about 10 gsm and about 25 gsm. The fluid distribution material also includes a nonwoven layer laminated to the second side of the formed film layer. The nonwoven layer includes a plurality of fibers attached to the formed film layer at the land areas and has a basis weight of between about 10 gsm and about 15 gsm. The fluid management system also includes a topsheet attached to the fluid distribution material. The first side of the formed film layer faces the topsheet.

In an embodiment, the fluid distribution material has a rewet value of less than 0.075 grams in accordance with the Rewet Test Method.

In an embodiment, the topsheet includes an apertured formed film.

In an embodiment, the topsheet includes a nonwoven web.

In an embodiment, the topsheet includes a laminate.

According to an aspect of the invention, there is provided an absorbent article that includes a topsheet, a backsheet, an absorbent material in between the topsheet and the backsheet, and a fluid distribution material in between the topsheet and the absorbent core. The fluid distribution material includes a formed film layer having a first side and a second side opposite the first side. The formed film layer includes a plurality of apertured protuberances arranged in a pattern having 10 to 40 protuberances per linear inch. Each of the protuberances includes a continuous sidewall extending from the first side and contacting the topsheet, and the second side has a plurality of apertures aligned with the plurality of apertured protuberances, and land areas in between the apertures. The formed film layer having a basis weight of between about 10 gsm and about 25 gsm. The fluid distribution material also includes a nonwoven layer laminated to the second side of the formed film layer. The nonwoven layer includes a plurality of fibers attached to the formed film layer at the land areas, and has a basis weight of between about 10 gsm and about 15 gsm.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Figure 1:
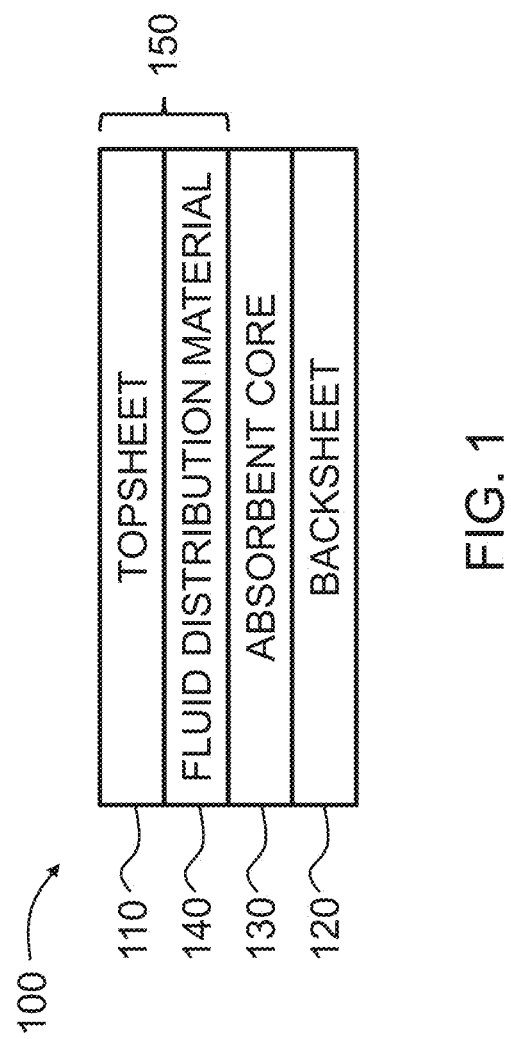
FIG. 1 is a schematic representation of an absorbent article in accordance with embodiments of the invention.

Various embodiments of the present invention will now be highlighted. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

Glossary

As used herein, the expression "absorbent articles" and "absorptive devices" denote articles that absorb and contain body fluids and other body exudates. More specifically, an absorbent article/absorptive device includes garments that are placed against or in proximity to the body of a wearer to absorb and contain the various exudates discharged from a body. Non-limiting examples of absorbent articles include, but are not limited to feminine hygiene products, baby diapers, adult incontinence products, and bandages.

Throughout this description, the term "web" refers to a material capable of being wound into a roll. Webs can be film webs, nonwoven webs, laminate webs, apertured laminate webs, etc. The face of a web refers to one of its two dimensional surfaces, as opposed to one of its edges.

The term "composite web" or "composite material" refers to a web that comprises two or more separate webs that are attached to each other in a face to face relationship. The attachment can be through the edges of the component webs, although the component webs lie in a face to face relationship with each other, or the attachment can be at particular spot locations across the component webs, or the attachment can be continuous.

The term "film" or "polymer film" in this description refers to a web made by extruding a molten curtain or sheet of thermoplastic polymeric material by a cast or blown extrusion process and then cooling the sheet to form a solid polymeric web. Films can be monolayer films, coextruded films, coated films, and composite films.

"Coated films" are films comprising a monolayer or coextruded film that are subsequently coated (for example, extrusion coated, impression coated, printed, or the like) with a thin layer of the same or different material to which it is bonded.

"Composite films" are films comprising more than one film where the at least two films are combined in a bonding process. Bonding processes may incorporate adhesive layers between the film layers.

Throughout this description, the expression "apertured films" denotes films that have a plurality of holes that extend from a first surface of the film to a second surface of the film.

A "two-dimensional apertured film" is a film in which no three-dimensional structure exists in the holes, which then connect the second surface of a flat film to the first surface of the film.

A "formed film" or a "three-dimensional film" is a film with protuberances, protrusions, or extended cells extending from at least one side thereof, and an "apertured formed film" or a "three-dimensional apertured film" is a film in which a three-dimensional structure exists in the apertures (e.g., the apertures have a depth that is thicker than the thickness of the film), or the protuberances or protrusions or extended cells have apertures therethrough.

The term "protuberance" as used herein refers to a three-dimensional member comprising an apertured base portion located in the plane of the first surface of the film and a sidewall portion extending generally in the direction of the second surface of the film. Each base portion has an associated sidewall portion. Sidewall portions terminate in "ends" located in the plane of the second surface of the film. The ends of the protuberances may be apertured or unapertured.

"Apertured protuberance" as used herein refers to a protuberance that has an aperture at its base portion or proximal end in the plane of the second surface, as well as its distal or protubered end. The apertures in the base portions of the protuberances, also called "primary apertures," may be in the shape of polygons, for example squares, hexagons, pentagons, ellipses, circles, ovals, or slots, in a regulated or random pattern. In an embodiment, the apertures may be in the shape of a boat, as described in, for example, U.S. Pat. No. 7,198,836, which is incorporated herein by reference.

The apertured distal or protubered ends are called "secondary apertures," and may be in the shape of polygons, e.g., squares, hexagons, pentagons, ellipses, circles, ovals, slots, or boats. The sidewall portion of the apertured protuberance extends from the primary aperture to the secondary aperture.

The term "nonwoven" means a web comprising a plurality of fibers. The fibers may be bonded to each other or may be unbonded. The fibers may be staple fibers or continuous fibers or filaments. The fibers may comprise a single material or may comprise a multitude of materials, either as a combination of different fibers or as a combination of similar fibers with each comprised of different materials.

As used herein, "nonwoven web" is used in its generic sense to define a generally planar structure that is relatively flat, flexible and porous, and includes staple fibers or continuous fibers or filaments. The nonwoven web may be the product of any process for forming the same, such as nonwoven spunbond and melt blown nonwoven webs. The nonwoven web may include a composite or combination of webs. The nonwoven web may comprise any polymeric material from which a fiber can be produced and/or may comprise cotton or other natural fibers. In an embodiment, the nonwoven web may be a spunbond material, made of polypropylene fiber. Fibers that comprise different polymers may also be blended. In an embodiment, the fibers may be so-called bi-component ("bi-co") fibers that comprise a core of one material and a sheath of another material.

The term "forming structure" or "screen" as used herein refers to a three-dimensional molding apparatus that comprises indentations used to form protuberances, extended cells or apertures in films, or protuberances in nonwoven webs. In an embodiment, forming structures comprise tubular members, having a width and a diameter. In alternative embodiments, forming structures may comprise belts having a width and a length. The transverse direction is the direction parallel to the width of the forming structure. The machine direction is the direction parallel to the direction of rotation of the forming structure, and is perpendicular to the transverse direction.

As used herein, the term "activating" or "activation" refers to a process of stretching a material beyond a point where its physical properties are changed. In the case of a nonwoven web, sufficient activation of the web will result in the nonwoven web being more extensible and/or improving its tactile properties. In an activation process, forces are applied to a material causing the material to stretch. Polymer films and nonwoven webs may be mechanically activated, for example. Mechanical activation processes comprise the use of a machine or apparatus to apply forces to the web to cause stretching of the web to an extent sufficient to cause permanent deformation of the web. Methods and apparatus used for activating webs of materials include, but are not limited to, activating the web through intermeshing gears or plates, activating the web through incremental stretching, activating the web by ring rolling, activating the web by tenter frame stretching, canted wheel stretchers or bow rollers, and activating the web in the machine direction between nips or roll stacks operating at different speeds to mechanically stretch the components, and combinations thereof.

Embodiments of the Invention

FIG. 1 schematically illustrates an absorbent article 100 in accordance with embodiments of the invention. As illustrated, the absorbent article 100 includes a topsheet 110, a backsheet 120, and an absorbent core 130 positioned in between the topsheet 110 and the backsheet 120. The absorbent article 100 also includes a fluid distribution material 140 positioned in between the topsheet 110 and the absorbent core 130.

The topsheet 110, which may be in the form of a two-dimensional or three-dimensional apertured film, a nonwoven web, or a laminate of an apertured film and a nonwoven web, is permeable to fluids and is configured to face the user wearing the absorbent article 100 and contact the user's skin. The topsheet 110 receives insults of fluid from the user, and the fluid passes through the topsheet 110 to the fluid distribution material 140. The fluid distribution material 140, embodiments of which are described in further detail below, is also permeable and is configured to receive the fluid from the topsheet 110 and distribute the fluid to the absorbent core 130. The absorbent core 130, which includes absorbent materials, receives the fluid from the fluid distribution material 140 and stores the fluid until the absorbent article 100 is discarded. The backsheet 120, which is impermeable to liquid and may be in the form of a polymer film or laminate of a polymer film and nonwoven web, prevents liquid and other body exudates from leaking out of the bottom side of the absorbent core 130. The backsheet 120 may be breathable so that air, but not liquid, may pass through.

In an embodiment, the topsheet 110 and the fluid distribution material 140 may be integrally formed as a fluid management system 150. For example, the topsheet 110 and the fluid distribution material 140 may be in a face to face relationship and attached to each other at their peripheries, or may be attached to each other at a plurality of locations, or continuously, across the webs to form a composite web. Such attachment may be achieved with one or more adhesives, or by thermal bonding, or by ultrasonic bonding, or by any other attachment means known in the art. In an embodiment, the absorbent article 100 may not include a topsheet 110. If so, the fluid distribution material 140 may function by itself as the fluid management system and be configured to be in contact with the user wearing the absorbent article 100.

Figure 2:
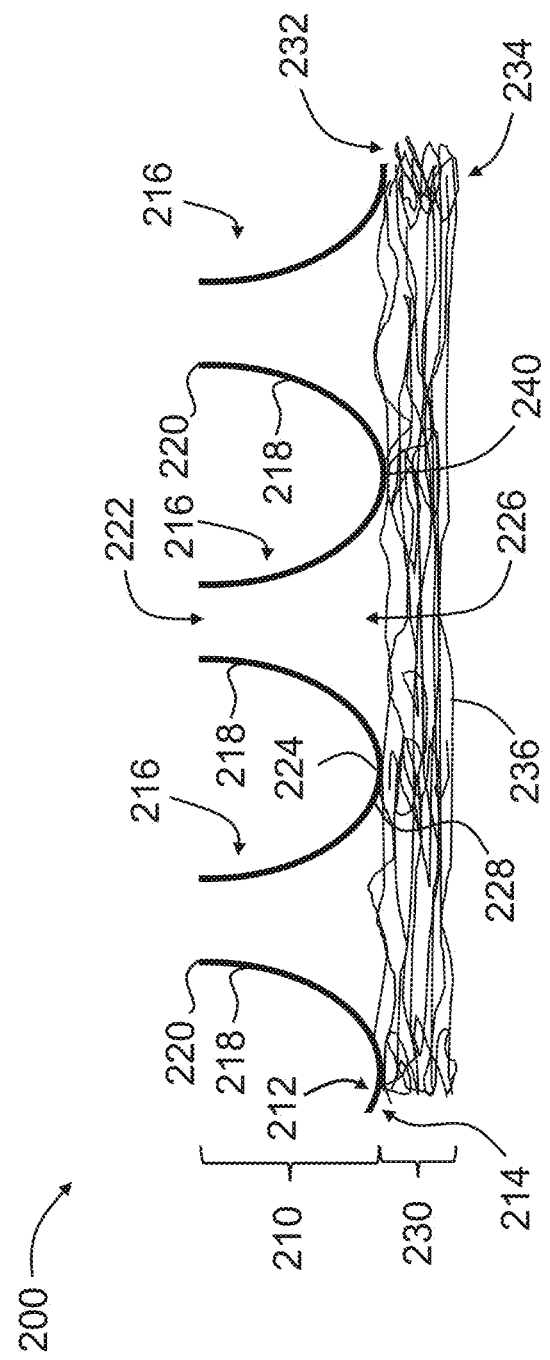
FIG. 2 is a schematic enlarged cross-sectional side view of a portion of a fluid distribution material of the absorbent article of FIG. 1 in accordance with embodiments of the invention.

FIG. 2 schematically illustrates a cross-section of a fluid distribution material 200, which may be used as the fluid distribution material 140 of FIG. 1, in accordance with embodiments of the invention. As illustrated, the fluid distribution material 200 includes a formed film layer 210 and a nonwoven layer 230. The formed film layer 210 has a first side 212 and a second side 214 that is opposite the first side 212. The formed film layer 210 includes a plurality of apertured protuberances 216. Each of the apertured protuberances 216 includes a continuous sidewall 218 extending from the first side 212 of the formed film layer 210 to a distal end 220 that includes a secondary aperture 222, as illustrated. The first side 212 of the formed film layer 210 also includes land areas 224 in between the apertured protuberances 216.

The second side 214 of the formed film layer 210 has a plurality of primary apertures 226 aligned with the plurality of protuberances 216. As such, the primary apertures 226 in the second side 214 of the formed film layer 210 are also considered to be proximal apertures 226 of the apertured protuberances 216, while the secondary apertures 222 at the distal ends 220 of the apertured protuberances 216 may also be considered to be distal apertures 222 of the apertured protuberances 216. The second side 214 of the formed film layer 210 also includes land areas 228 in between the proximal apertures 226.

In an embodiment, the apertured protuberances 216 may be arranged in a pattern having about 10 to about 40 protuberances per linear inch or "mesh," i.e., about 10 mesh to about 40 mesh. The pattern may be a hexagonal pattern, a square pattern, a staggered pattern, or any other type of pattern or design. In an embodiment, the apertured protuberances 216 may be arranged in a 10-25 mesh pattern. In an embodiment, the apertured protuberances 216 may be arranged in about an 11 mesh pattern. In an embodiment, the apertured protuberances 216 may be arranged in about a 22 mesh pattern. In an embodiment, the apertured protuberances 216 may be arranged in a 40 mesh pattern. In an embodiment, the proximal apertures 226 may be hexagonal in shape and have approximately the same size. In an embodiment, the proximal apertures 226 may have different sizes and/or shapes, as described in further detail below.

The polymer of the formed film layer 210 may include one or more polyolefins, including but not limited to polyethylene, ultra-low density polyethylene, low density polyethylene, linear low density polyethylene, linear medium density polyethylene, high density polyethylene, polypropylene, ethylene-vinyl acetates, metallocene, as well as other polymers. Other polymers include but are not limited to elastomeric polymers, including but not limited to polypropylene based elastomers, ethylene based elastomers, copolyester based elastomers, olefin block copolymers, styrenic block copolymers and the like, or combinations thereof. Additives, such as surfactants, fillers, colorants, opacifying agents and/or other additives known in the art may also be used in the formed film layer 210.

Returning to FIG. 2, the nonwoven layer 230 has a first side 232 and a second side 234 opposite the first side 232. In the illustrated embodiment, the first side 232 of the nonwoven layer 230 contacts the second side 214 of the formed film layer 210. The nonwoven layer 230 includes a plurality of fibers 236.

Nonwoven webs that may be used for the nonwoven layer 230 may be formed from many processes, including but not limited to spunbonding processes, melt-blowing processes, hydroentangling processes, spunlacing processes, air-laying, and bonded carded web processes, or combinations thereof, as are known in the nonwoven art. In an embodiment, the nonwoven layer 230 may be a spunbonded nonwoven web. In an embodiment, the fibers 236 in the nonwoven layer 230 may be polypropylene fibers. In an embodiment, the nonwoven layer 230 may include natural fibers, such as cotton.

In an embodiment, the formed film layer 210 is attached to the nonwoven layer 230 at bond sites 240 where the first side 232 of the nonwoven layer 230 contacts the land areas 228 of the second surface 214 of the formed film layer 210. In an embodiment, the fibers 236 at the bond sites 240 are embedded into the land areas 228 of the formed film layer 210, which may be accomplished by a vacuum formed lamination process, as described in further detail below. The bond sites 240 are contemplated to be distributed in a pattern, commensurate with some or all of the land areas 228.

Figure 3:
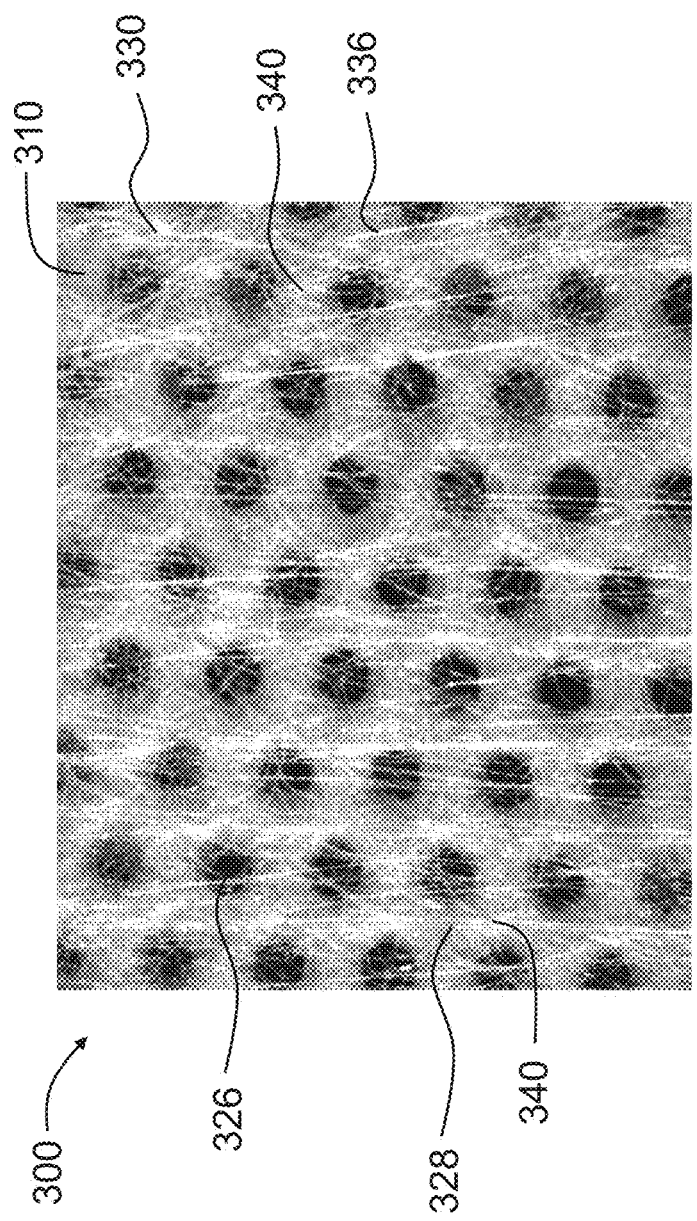
FIG. 3 is an enlarged photograph of a view of one side of an embodiment of the fluid distribution material of FIG. 2.

FIG. 3 is an enlarged photograph of one side of a fluid distribution material 300 in accordance with an embodiment of the invention, which may be used as the fluid distribution material 140 of FIG. 1. As illustrated, the fluid distribution material 300 includes a formed film layer 310 and a nonwoven layer 330 on top of the formed film layer 310. The formed film layer 310 includes apertures 326 and land areas 328 extending between the apertures 326. The nonwoven layer 330 includes a plurality of continuous fibers 336 that extend across the land areas 328 and the apertures 326 of the formed film layer 310. The continuous fibers 336 are attached to the land areas 328 at bond sites 340.

Figure 4:
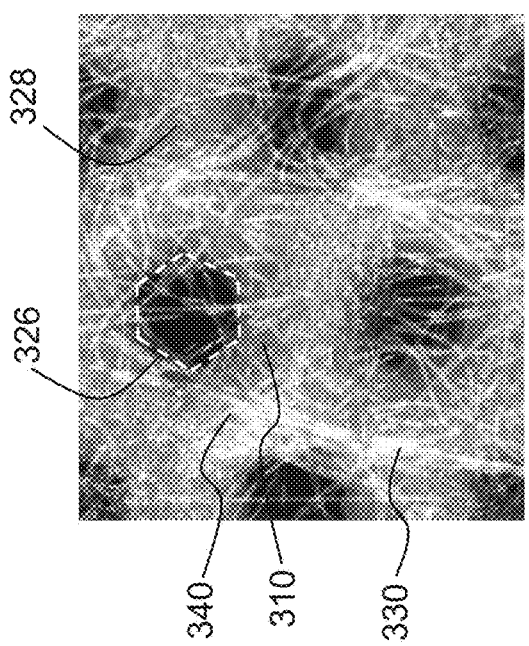
FIG. 4 is an enlarged photograph of a portion of the fluid distribution material of FIG. 3.

A closer view of the apertures 326, land areas 328, and bond sites 340 is illustrated in FIG. 4.

Figure 5:
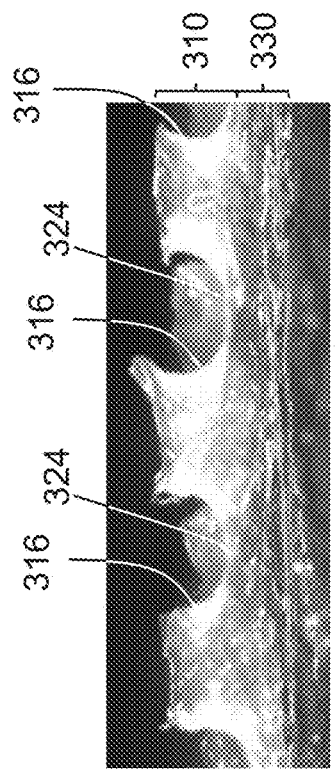
FIG. 5 is an enlarged photograph of a partial cross-sectional side view of the fluid distribution material of FIGS. 3 and 4.

FIG. 5 is an enlarged photograph of a partial cross-sectional view of the fluid distribution material 300 of FIG. 3 with the formed film layer 310 on top of the nonwoven layer 330. FIG. 5 also shows a plurality of apertured protuberances 316 with land areas 324 extending in between adjacent apertured protuberances 316. The apertured protuberances 316 (FIG. 5) and corresponding apertures 326 (FIGS. 3 and 4) are arranged in a 22 mesh pattern, and each of the apertures 326 has a hexagonal ("hex") shape, as represented by the dashed white lines in FIG. 4.

Figure 6:
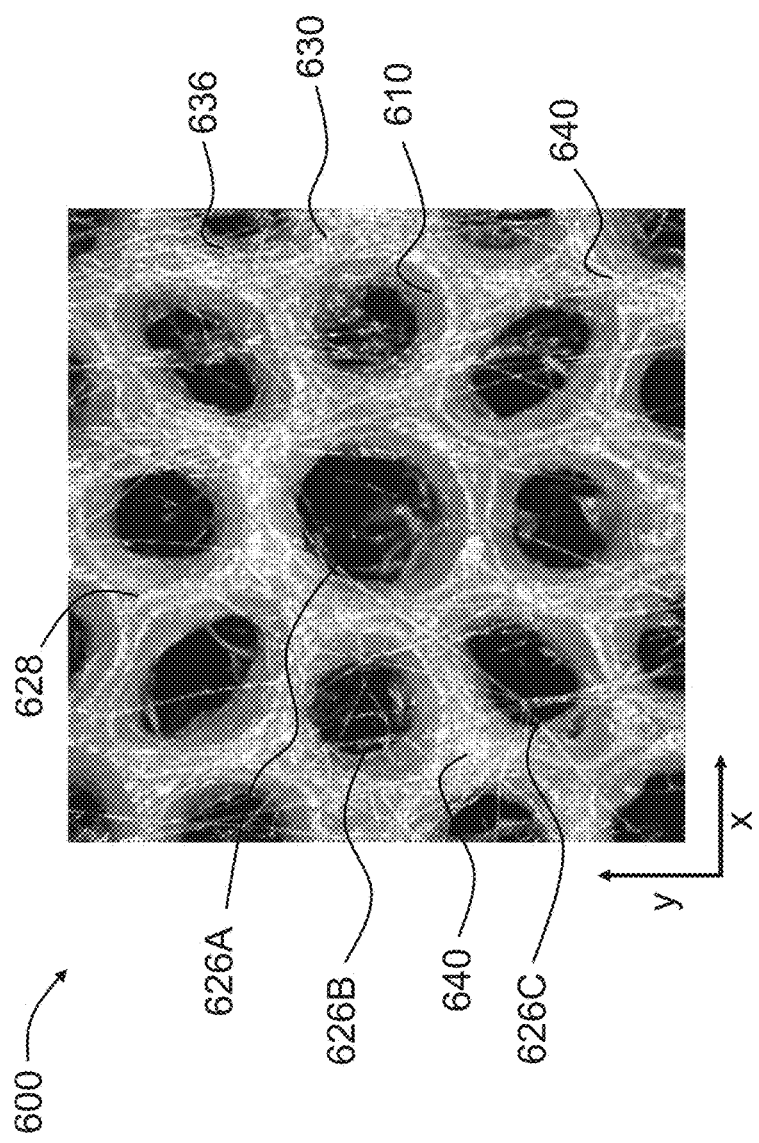
FIG. 6 is an enlarged photograph of a view of one side of an embodiment of the fluid distribution material of FIG. 2.

FIG. 6 is an enlarged photograph of one side of a fluid distribution material 600 in accordance with an embodiment of the invention, which may be used as the fluid distribution material 140 of FIG. 1. As illustrated, the fluid distribution material 600 includes a formed film layer 610 and a nonwoven layer 630 on top of the formed film layer 610. The formed film layer 610 includes three different types of apertures 626A, 626B, 626C, and land areas 628 extending between the apertures 626A, 626B, 626C. As illustrated, the apertures 626A, 626B, 626C are arranged in a pattern that resembles a blossom or flower, with a center, substantially-round aperture 626A being surrounded by four smaller, substantially-round apertures 626B and four elliptical or oval-shaped apertures 626C, each having their major axis extending at approximately 45 degree angles relative to an x-y grid. The circular apertures 626A, 626B may have a mesh count of about 15 apertures per linear inch (i.e., 15 mesh) in the x direction and the y direction. The nonwoven layer 630 includes a plurality of continuous fibers 636 that extend across the land areas 628 and the apertures 626A, 626B, 626C of the formed film layer 610. The continuous fibers 636 are attached to the land areas 628 at bond sites 640.

Figure 7:
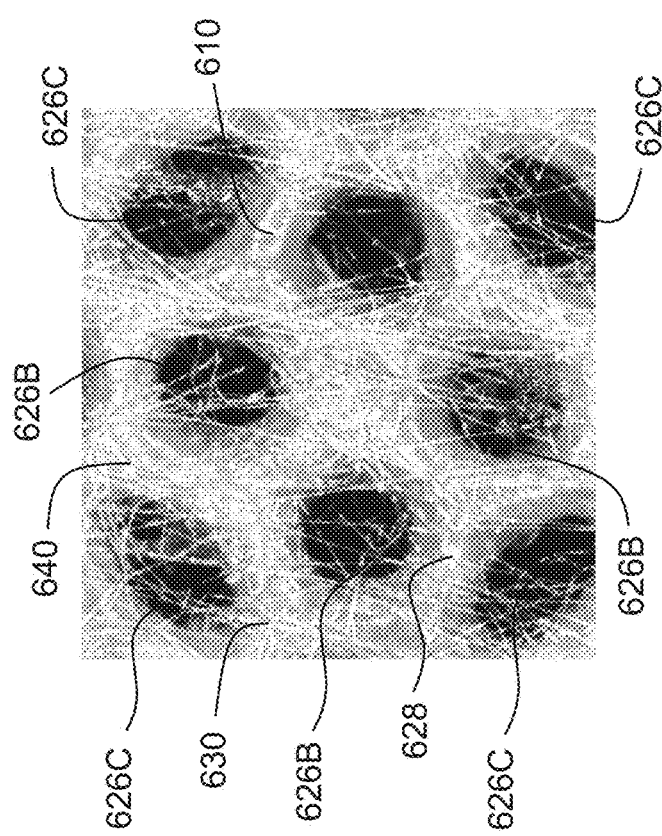
FIG. 7 is an enlarged photograph of a portion of the fluid distribution material of FIG. 6.

A closer view of the apertures 626B, 626C, land areas 628, and bond sites 640 is illustrated in FIG. 7.

Figure 8:
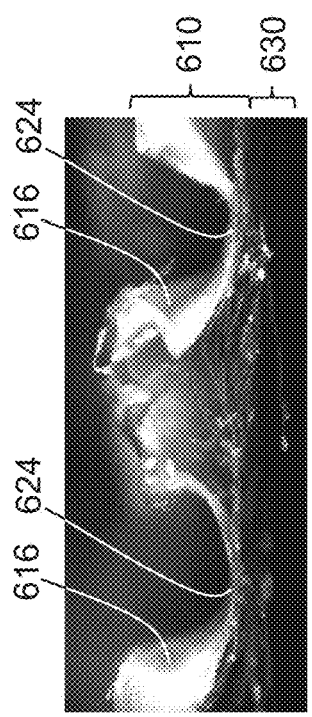
FIG. 8 is an enlarged photograph of a partial cross-sectional side view of the fluid distribution material of FIGS. 6 and 7.

FIG. 8 is an enlarged photograph of a partial cross-sectional view of the fluid distribution material 600 of FIG. 6 with the formed film layer 610 on top of the nonwoven layer 630. FIG. 6 also shows a plurality of apertured protuberances 616 with land areas 624 extending in between adjacent apertured protuberances 616.

Figure 9:
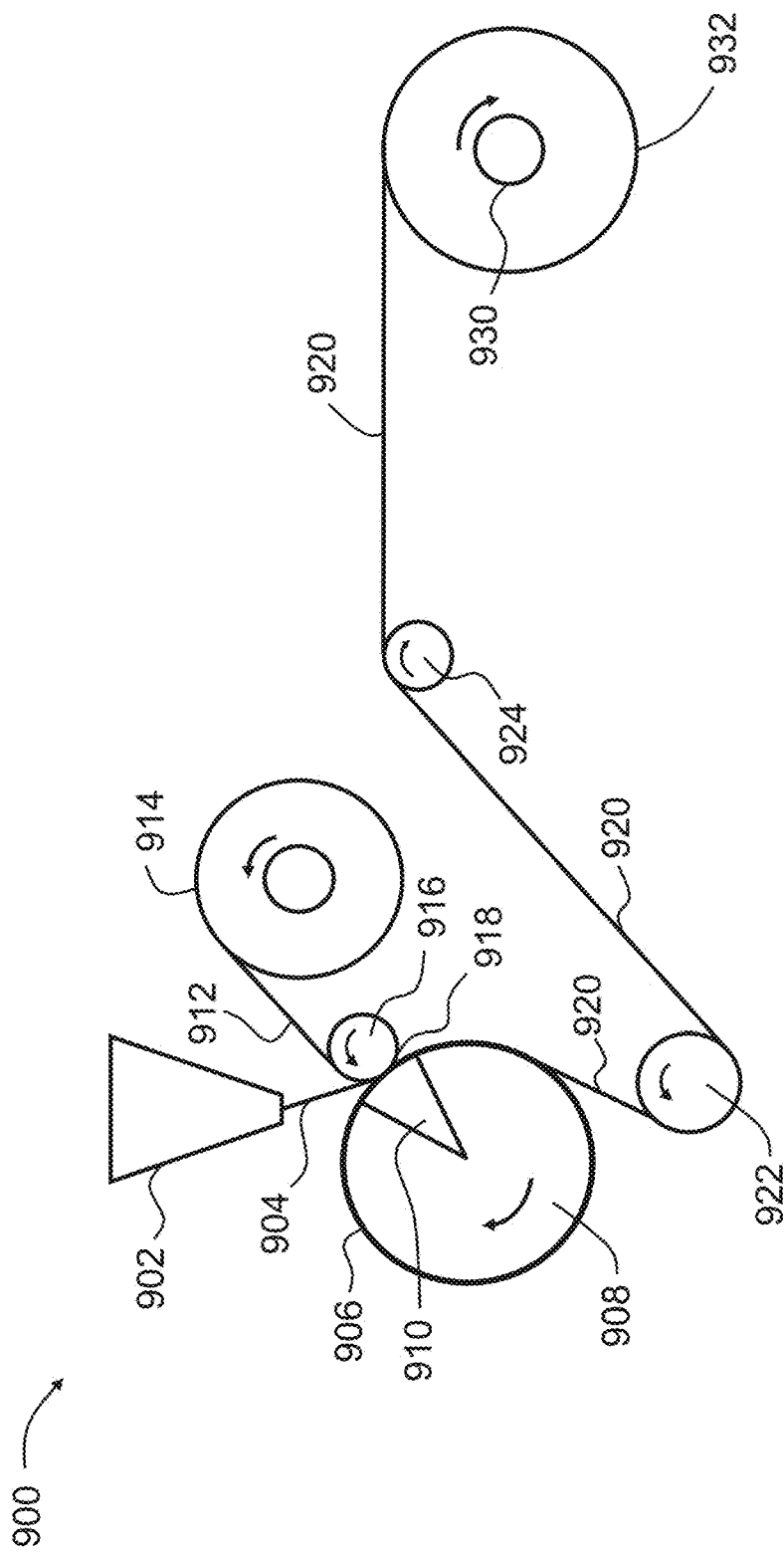
FIG. 9 is a schematic representation of an apparatus for manufacturing the fluid distribution material in accordance with embodiments of the invention.

FIG. 9 schematically illustrates an apparatus 900 that may be used to manufacture the fluid distribution materials of embodiments of the invention described herein. As illustrated, an extrusion die 902 extrudes polymer melt curtain 904 onto a forming structure 906 that rotates about a cylinder 908 that has a vacuum slot 910 through which a vacuum is pulled. The polymer melt curtain 904 may include, for example, one or more polyolefin materials and a surfactant, as well as one or more additives, such as a colorant. A nonwoven web 912 is unwound from a roll 914 over a laminating roller 916 and directed to the melt curtain 904 while the melt curtain 904 is still molten at an impingement point 918 between the rotating forming structure 906 and the laminating roller 916.

The fibers of the nonwoven web 912 adjacent to the melt curtain 904 embed in the surface of the melt curtain 904 as the two layers cross over the vacuum slot 910 together, where the apertured protuberances are formed in the polymer web (i.e., the solidified melt curtain 904) in substantially the same pattern that is provided by the forming structure 906. As the polymer web (which solidifies to form, for example, the formed film layer 210 of FIG. 2) is apertured, air flow is initiated through the apertured protuberances (e.g., 216) which cools and solidifies the apertured protuberances (e.g., 216). The polymer web is also cooled by the forming structure 906 as the fibers (e.g., 236) of the nonwoven are embedded in the land areas (e.g., 228) between the apertured protuberances (e.g., 216) so that the nonwoven is bonded to the formed film layer (e.g., 210) at the land areas (e.g., 228). The resulting vacuum formed laminate 920 is pulled off of forming structure 906 by a peel roller 922 and travels to one or more subsequent rollers 924 until it may be wound by a winder 930 into a roll 932. Additional rollers and/or other pieces of equipment may be used in the apparatus 900.

The illustrated embodiment is not intended to be limiting in any way. For example, in an embodiment, the apparatus 900 may also include additional equipment, such as intermeshing gears that may be used to activate the fluid distribution material in the machine direction or the transverse direction, if desired. Other equipment that may be included in the apparatus 900 include, but are not limited to, corona treatment apparatus, printers, festooning equipment, spooling equipment, and additional processing equipment that may emboss or provide additional apertures to the vacuum formed laminate 920.

FIGS. 10-13 schematically illustrate how the fluid distribution material 200 handles a fluid insult 1000 and distributes the fluid insult 1000 to a substrate 240 located beneath the fluid distribution material 200, which may be an absorbent core, as described above, or may be a blotter paper used during testing, as described below. Although a topsheet may be positioned above the fluid distribution material 200, as described above, a topsheet is not illustrated in FIGS. 10-13 for simplicity.

Figure 10:
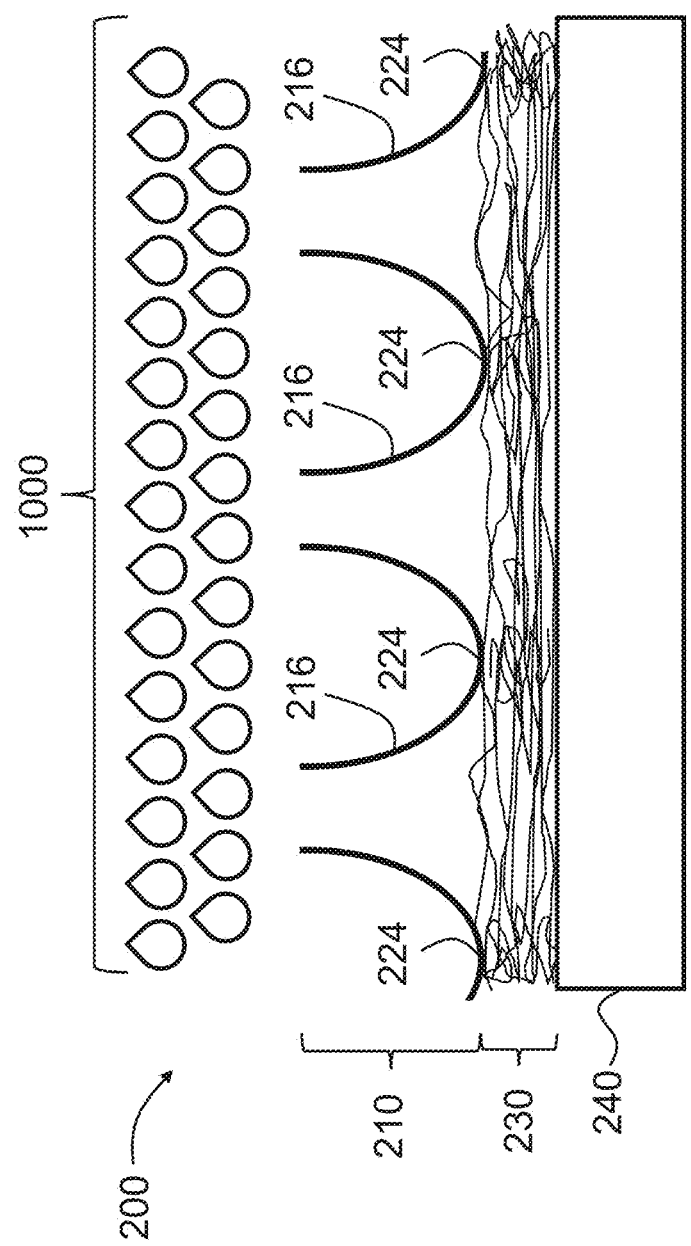
FIG. 10 is a schematic enlarged cross-sectional side view of the portion of the fluid distribution material of FIG. 2 with an insult being applied to the fluid distribution material from above.
Figure 11:
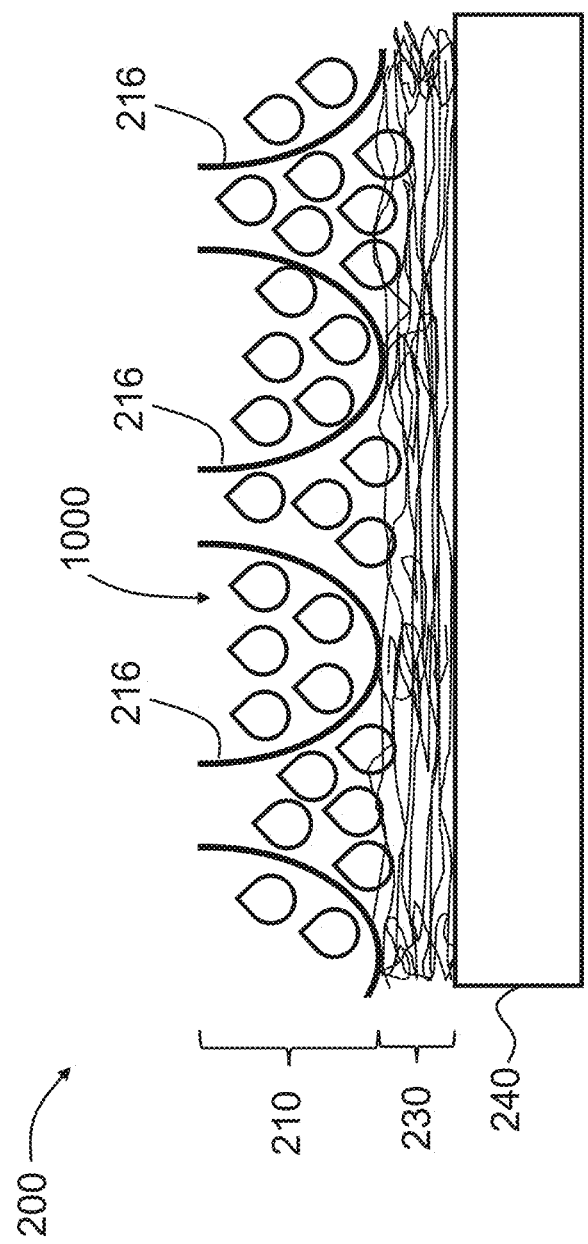
FIG. 11 is a schematic enlarged cross-sectional side view of the portion of the fluid distribution material and insult of FIG. 10 with the insult being handled by the fluid distribution material.
Figure 12:
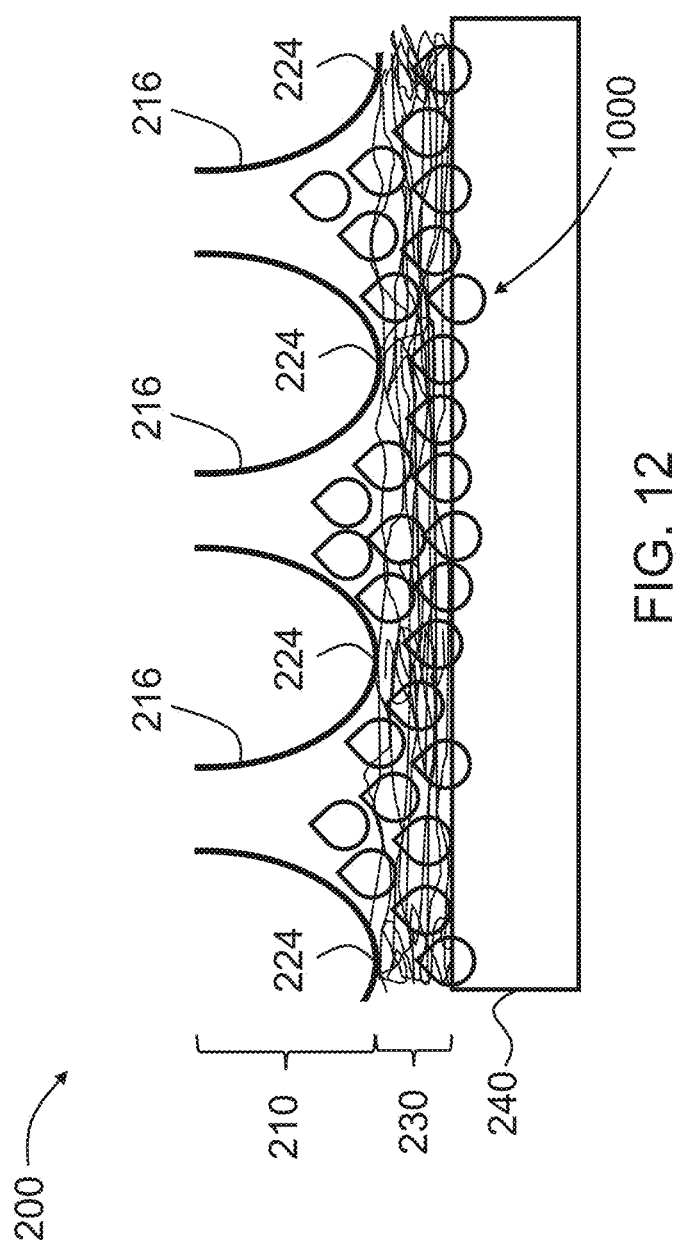
FIG. 12 is a schematic enlarged cross-sectional side view of the portion of the fluid distribution material and insult of FIGS. 10 and 11 with the insult being further handled by the fluid distribution material.
Figure 13:
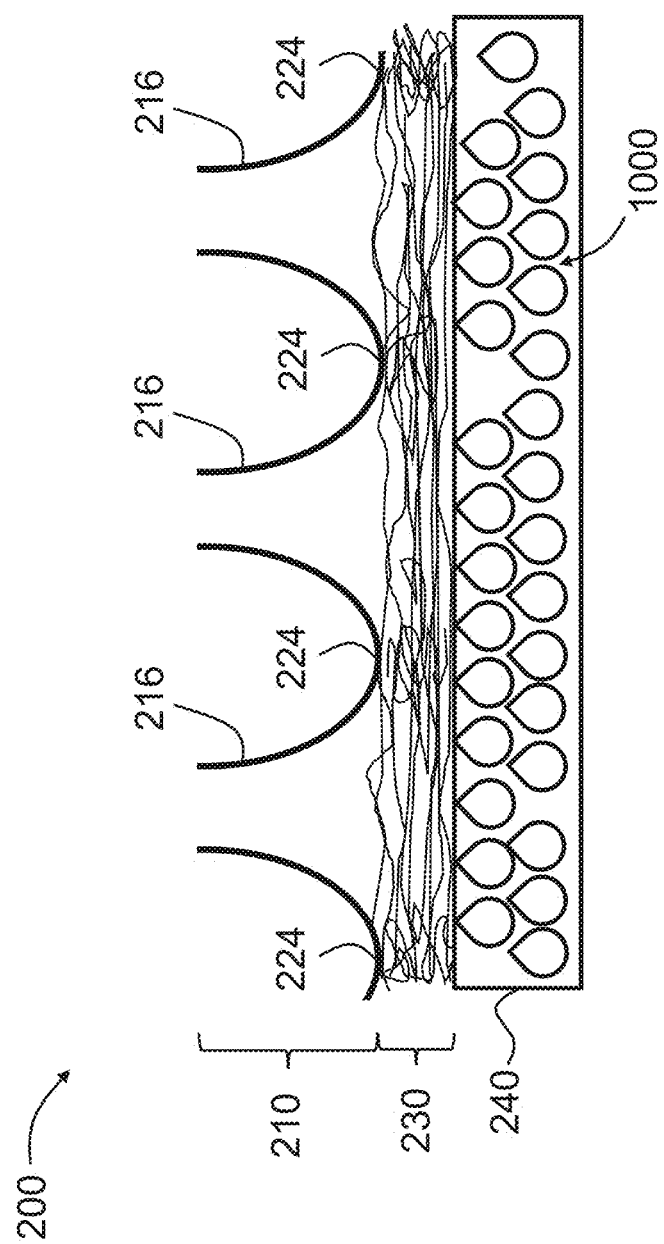
FIG. 13 is a schematic enlarged cross-sectional side view of the portion of the fluid distribution material and insult of FIGS. 10, 11 and 12 after the insult has passed through the fluid distribution material and into an underlying material.

As illustrated in FIG. 10, the fluid insult 1000, which is schematically represented as a plurality of droplets, is introduced to the formed film layer 210 side of the fluid distribution material 200. FIG. 11 illustrates the initial phase of fluid strikethrough. Portions of the insult 1000 are able to enter the unobstructed apertured protuberances 216 and pass through to the nonwoven layer 230, while other portions of the insult 100 are trapped on the land areas 224 between the apertured protuberances 216. As the initial fluid that entered the apertured protuberances 216 drains into and spreads along the nonwoven layer 230, and even passes through to the substrate 240 below, the fluid in between the apertured protuberances 216 is siphoned into the apertured protuberances 216, due to the surface tension of the fluid and the hydrophilic nature of the formed film layer 210, until all or substantially all of the fluid passes through the formed film layer 210 of the fluid distribution material 200, as illustrated in FIGS. 12 and 13. Although it is desirable to have the nonwoven layer 230 to also be hydrophilic, the nonwoven layer 230 may in some embodiments be hydrophobic.

Examples

A series of fluid distribution materials were created using the apparatus 900 described above. A hydrophilic spunbond nonwoven, manufactured by Fitesa of Simpsonville, S.C., comprising a plurality of polypropylene fibers and having a nominal basis weight of 12 grams per square meter (gsm) was used as the nonwoven web 912. A blend of low density polyethylene, high density polyethylene, titanium dioxide and surfactant was extruded through the extrusion die 902 to create the melt curtain 904, which was cast onto different forming structures 906 as the nonwoven web 912 was fed into the impingement point 918 to create laminates 920 with formed film layers having different patterns of apertured protuberances and open areas. The formed film layers had a basis weight of about 18 gsm so that the laminates 920 had a total basis weight of about 30 gsm.

The open area, which is the percent area of the openings through the sample as compared to the total area of the sample, for each sample was measured using a computerized video device that includes a video camera, a microscope using a 24× magnification, and imaging software that measures contrast. A magnified image was taken of the sample when looking at the formed film layer side of the sample, and the video camera, which can discern the openings through the sample from solid portions of the sample via contrast, digitized the data to calculate the percent open area. Table I summarizes the laminated ("laminate") samples that were created, along with the respective open areas that were measured.

TABLE I

Fluid Distribution Material (Laminate) Samples

| "Laminate" Sample | Formed Film Layer Apertured Protuberance Pattern | Open Area (%) |
|---|---|---|
| 1 | 11 mesh hexagonal | 5.4 |
| 2 | 22 mesh hexagonal | 5.5 |

TABLE I-continued

Fluid Distribution Material (Laminate) Samples

| "Laminate" Sample | Formed Film Layer Apertured Protuberance Pattern | Open Area (%) |
|---|---|---|
| 3 | 40 mesh hexagonal | 6.3 |
| 4 | 15 mesh blossom | 6.8 |

FIGS. 3-5 (described above) illustrate a portion of Sample 2 and FIGS. 6-8 (described above) illustrate a portion of Sample 4. As noted above, "mesh" refers to the number of apertures per linear inch, "hexagonal" refers to the shape of the apertures, and "blossom" refers to the pattern illustrated in FIG. 9 that has different sized and shaped apertures that are arranged in a blossom or flower pattern.

The same blend of materials and forming structures that were used to create the formed film layers for Samples 1-4 were used to create only apertured formed films having a basis weight of about 18 gsm, which is the same basis weight of the formed film layers of Samples 1-4. The open area for each film (absent the nonwoven web 912) was measured under a microscope using a 24× magnification and imaging software that measures contrast. Each of the film samples was placed on top of (but not bonded in any way to) the same spunbond nonwoven web 912 that was used to create the laminates for Samples 1-4 (i.e., a 12 gsm spunbond polypropylene nonwoven web manufactured by Fitesa of Simpsonville, S.C.), with the apertured protuberances extending in a direction away from the nonwoven web to form "stacks" of formed films and nonwoven webs. Table II summarizes the comparative stack ("stack") samples that were created, along with the respective open areas that were measured in the same manner as the open areas of the laminate samples, with the formed film side of the stack facing the video camera.

TABLE II

Comparative Formed Film/Nonwoven "Stack" Samples

| "Stack" Sample | Formed Film Apertured Protuberance Pattern | Open Area (%) |
|---|---|---|
| 5 | 11 mesh hexagonal | 1.4% |
| 6 | 22 mesh hexagonal | 2.6% |
| 7 | 40 mesh hexagonal | 2.4% |
| 8 | 15 mesh blossom | 2.1% |

Each of the stack samples had an open area lower than the open area of a laminate sample having the same apertured protuberance pattern, which indicates that the fibers in the nonwoven layers of the laminate samples may have spread apart at the locations of the apertured protuberances to provide a higher open area. Without being bound by theory (and returning to FIG. 2), it is postulated that during the vacuum forming lamination process, air being pulled through the nonwoven layer 230 and the formed film layer 210 may cause the fibers 236 located adjacent the proximal apertures 226 to separate and gather at a higher density at the land areas 228 where there is no air flow as the polymer in the formed film layer 210 cools on the forming structure. When the polymer in the formed film layer 210 solidifies, the fibers 236 of the nonwoven layer 230 are essentially locked in place at the bond sites 240 while the fibers 236 located adjacent the proximal apertures 226 remain spread apart.

Strikethrough Time and Rewet Testing

All samples were tested for suitability for use as a fluid distribution material in accordance with embodiments of the invention. Specifically, for each sample, strikethrough time and rewet, which is a measure of dryness, were determined for three different test specimens by a "Lister AC" fluid testing device, by Lenzing Technik GmbH & Co KG, Austria. The procedures for measuring strikethrough time ("Strikethrough Test Method") and rewet ("Rewet Test Method"), which are based on the principles outlined in EDANA test methods ERT 150.5-02 and ERT 151.3-02, respectively, will now be described. All of the test specimens and absorbent substrates, filter papers and pickup papers described below were conditioned at 23° C.±2° C. at 50%±5% relative humidity for 24 hours.

For the Strikethrough Test Method, each test specimen was cut into a 5"×5" (125 mm×125 mm) piece and placed over an absorbent substrate in the form of a stack of three (3) pieces of 4"×4" filter (blotter) paper. The test specimen was oriented so that the formed film layer faced upward and the nonwoven layer was in contact with the filter paper. A 500 g strikethrough plate with a 100 mm×100 mm base dimension and an orifice with electrodes extending into the orifice was placed on top of the test specimen. A 5 mL sample of fluid that simulates urine and consists of a solution of 9.0 g/l of analytical grade sodium chloride in deionized water, with a surface tension of 70±2 mN/m at 23±2° C., was dispersed into the orifice from a height of 30 mm above the surface of the test specimen. The fluid completed a circuit with the electrodes, which started a timer. When the fluid was completely struck through the orifice, the circuit was broken and the timer stopped, thereby registering the elapsed time or "strikethrough time" in seconds.

For the "Rewet Test Method," after the initial insult from the Strikethrough Test Method, an additional insult was dispensed to the center of the test specimen with the strikethrough plate still in place. The additional insult was based on the total insult (including the initial 5 mL insult from the Strikethrough Test Method) needed to fully saturate the underlying absorbent substrate and was calculated by multiplying the weight of the stack of three pieces of filter paper (when dry) by the load factor of the filter paper, and was determined to be 10 mL. The strikethrough plate was removed and a 4000 g rewet weight with a 100 mm×100 mm footing was placed on top of the test specimen to allow the fluid to thoroughly spread out into the absorbent substrate. Two pre-weighed 5"×5" pick up (blotter) papers were pressed against the surface of the test specimen with the rewet weight to create a pressure of about 0.50 psi, to simulate a toddler sitting on a diaper, for an additional two minutes. The wetted pickup papers were weighed. Any residual wetness in the test specimen is transferred to the pickup papers, and the difference between the pre-measured dry weight of the pickup papers and the wetted weight of the pickup papers is the "rewet value" in grams. The average strikethrough time and rewet value test results for three test specimens for each sample are listed in below in Table III.

TABLE III

Strikethrough Time and Rewet Test Results

| Sample | Description | Strikethrough Time (seconds) | Rewet Value (grams) |
|---|---|---|---|
| 1 | 11 mesh hexagonal laminate | 0.97 | 0.060 |
| 2 | 22 mesh hexagonal laminate | 1.47 | 0.052 |
| 3 | 40 mesh hexagonal laminate | 2.26 | 0.074 |
| 4 | 15 mesh blossom laminate | 1.52 | 0.059 |
| 5 | 11 mesh hexagonal stack | 0.98 | 0.104 |
| 6 | 22 mesh hexagonal stack | 1.57 | 0.076 |
| 7 | 40 mesh hexagonal stack | 2.54 | 0.158 |
| 8 | 15 mesh blossom stack | 1.36 | 0.107 |

Figure 14:
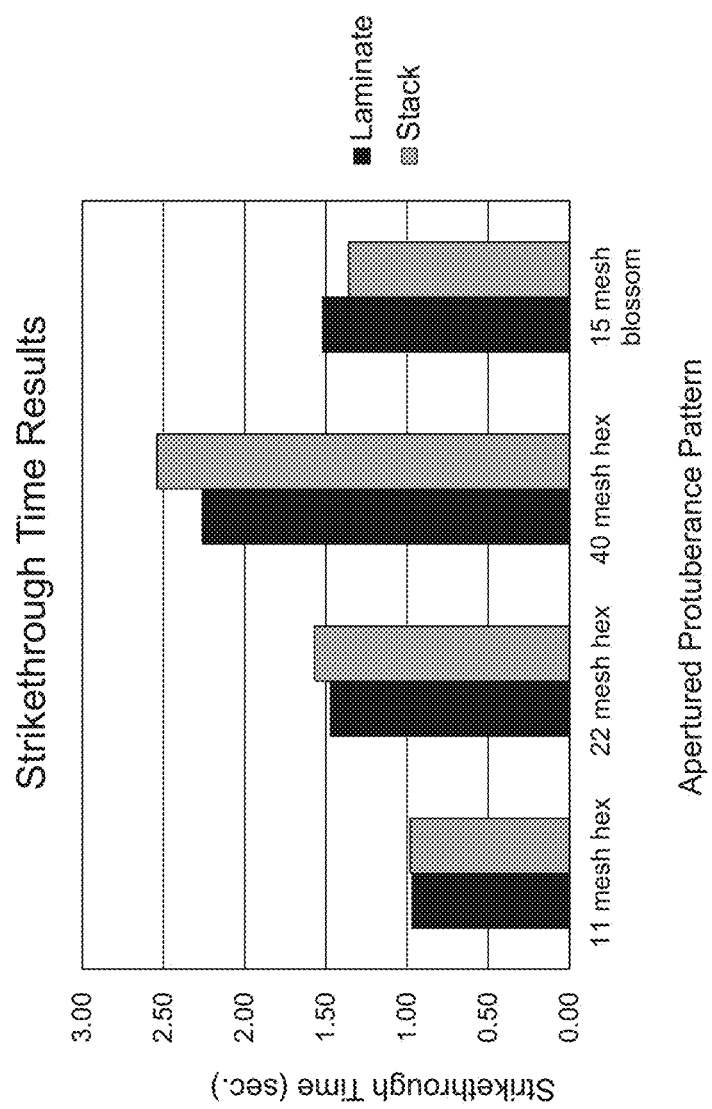
FIG. 14 is a plot of strikethrough testing results for embodiments of the invention and comparison samples.
Figure 15:
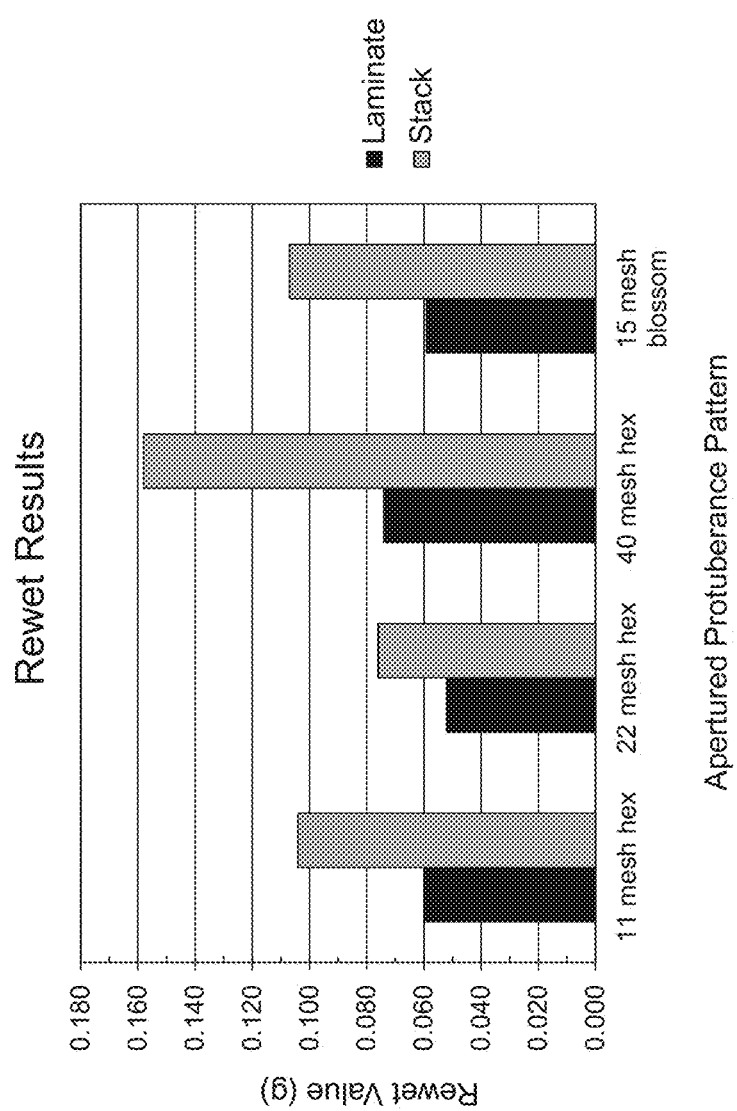
FIG. 15 is a plot of rewet testing results for embodiments of the invention and comparison samples.

The strikethrough time and rewet results are also plotted in FIGS. 14 and 15, respectively. As shown in FIG. 14, all of the laminate samples with hexagonal shaped apertures ("hex") had faster strikethrough times as compared to their corresponding stack samples. The laminate sample with the blossom pattern (Sample 4) had a slightly slower strikethrough time than its corresponding stack sample (Sample 8). As shown in FIG. 15, all of the laminate samples (Samples 1-4) had at least 30% lower rewet values than their corresponding stack samples (Samples 5-8), and each of the laminate samples (Samples 1-4) had rewet values of less than 0.075, while each of the stack samples (Samples 5-8) had rewet values greater than 0.075.

Compressibility Testing

All samples were also tested for thickness when under pressure so that the compressibility of the samples could be determined. Thicknesses were measured using a Testing Machines, Inc. Model 49-70 motorized low-load micrometer with an anvil having a diameter of 2 inches, a dead weight load of 298 grams (0.657 pounds), which is equivalent to an applied pressure of 0.21 psi, and a dwell time of 2-5 seconds. Multiple measurements were made for each sample at different locations across the sample, and the measurements for each sample were averaged to determine a baseline thickness measurement for each sample. Additional weight was added to the anvil to increase the applied pressure to 0.31 psi, 0.40 psi, 0.50 psi and 0.60 psi. 0.50 psi is commonly likened to the pressure exerted by a toddler sitting on a diaper. Multiple measurements were made for each sample at different locations across the sample at each pressure, and the measurements for each sample at each pressure were averaged. The results of the thickness testing under different applied pressures are listed in Table IV below.

TABLE IV

Thickness Under Applied Pressure Test Results

| Sample | Thickness (microns) @ 0.21 psi | Thickness (microns) @ 0.31 psi | Thickness (microns) @ 0.40 psi | Thickness (microns) @ 0.50 psi | Thickness (microns) @ 0.60 psi |
|---|---|---|---|---|---|
| 1 | 756 | 728 | 710 | 698 | 686 |
| 2 | 530 | 513 | 500 | 491 | 485 |
| 3 | 382 | 375 | 360 | 353 | 353 |
| 4 | 635 | 625 | 614 | 604 | 592 |
| 5 | 730 | 689 | 667 | 642 | 608 |
| 6 | 567 | 553 | 543 | 523 | 516 |
| 7 | 417 | 409 | 394 | 386 | 375 |
| 8 | 683 | 656 | 638 | 623 | 609 |

The results of the thickness testing under different pressures were used to calculate the compressibility of the samples a various pressures, using the thickness measurement at the lowest pressure (i.e., 0.21 psi) as the baseline. The compressibility of each sample was calculated for each of the 0.31 psi, 0.40 psi, 0.50 psi, and 0.60 psi applied pressures using the following equation (1):

$$\text{compressibility}(\%) = \frac{(\text{thickness}_{x\ psi} - \text{thickness}_{0.21\ psi})}{\text{thickness}_{0.21\ psi}} \times 100 \quad (1)$$

where x is the applied pressure, $\text{thickness}_{x\ psi}$ is the average thickness at the applied pressure, and $\text{thickness}_{0.21\ psi}$ is the average thickness at 0.21 psi applied pressure. The results are listed in the following Table V.

TABLE V

Compressibility Test Results

| Sample | Compressibility (%) @ 0.31 psi | Compressibility (%) @ 0.40 psi | Compressibility (%) @ 0.50 psi | Compressibility (%) @ 0.60 psi |
|---|---|---|---|---|
| 1 | 3.7 | 6.1 | 7.7 | 9.3 |
| 2 | 3.2 | 5.7 | 7.4 | 8.5 |
| 3 | 1.8 | 5.8 | 7.6 | 7.6 |
| 4 | 1.6 | 3.3 | 4.9 | 6.8 |
| 5 | 5.6 | 8.6 | 12.1 | 16.7 |
| 6 | 2.5 | 4.2 | 7.8 | 9.0 |
| 7 | 1.9 | 5.5 | 7.4 | 10.1 |
| 8 | 4.0 | 6.6 | 8.8 | 10.8 |

Figure 16:
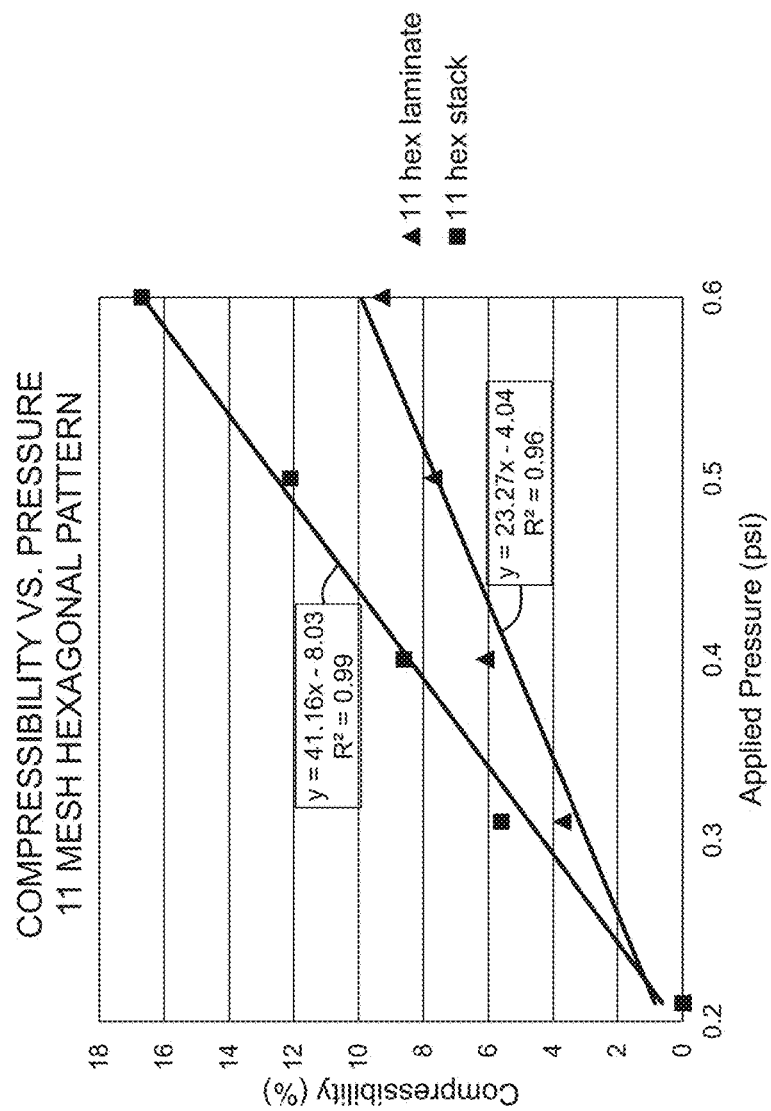
FIG. 16 is a plot of compressibility as a function of applied pressure for an embodiment of the fluid distribution material and a comparison sample.
Figure 17:
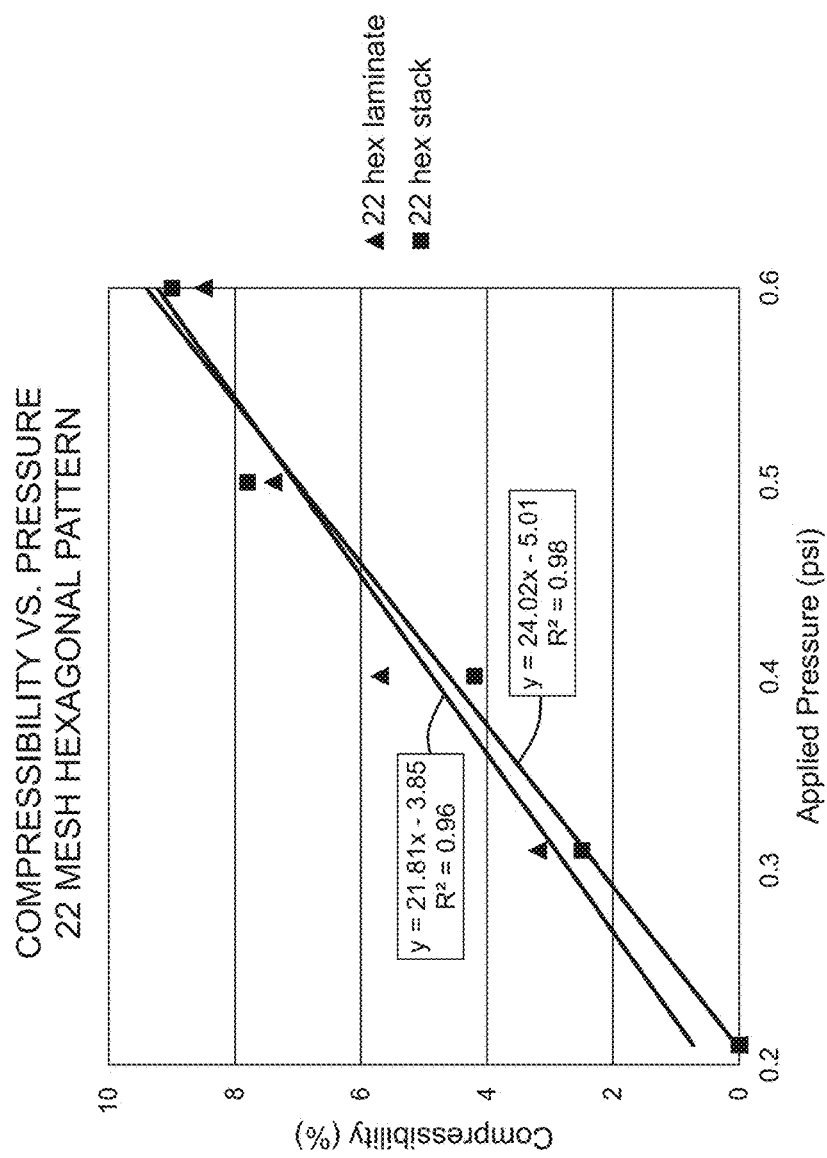
FIG. 17 is a plot of compressibility as a function of applied pressure for an embodiment of the fluid distribution material and a comparison sample.
Figure 18:
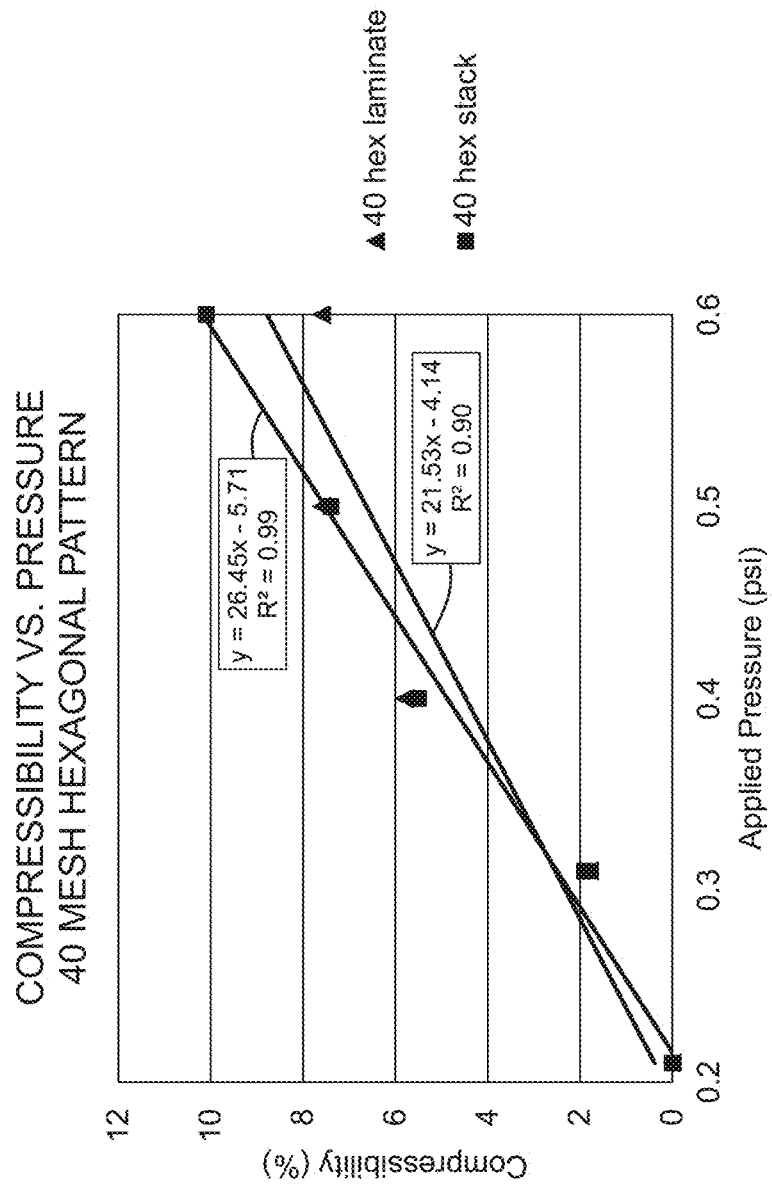
FIG. 18 is a plot of compressibility as a function of applied pressure for an embodiment of the fluid distribution material and a comparison sample.
Figure 19:
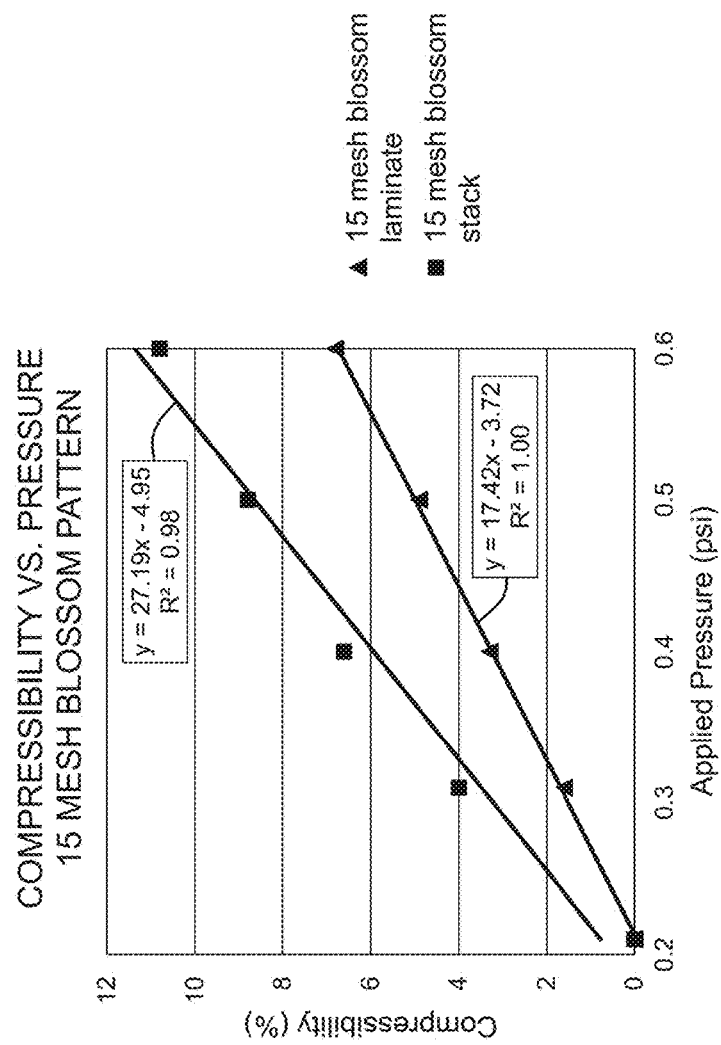
FIG. 19 is a plot of compressibility as a function of applied pressure for an embodiment of the fluid distribution material and a comparison sample.

The compressibility test results are also illustrated in FIGS. 16-19, with the baseline applied pressure (i.e. 0.21 psi) set to 0% for all samples. Specifically, FIG. 16 illustrates the results for Sample 1 (laminate) and Sample 5 (stack), which each had a formed film layer with apertured protuberances in the 11 mesh hexagonal ("hex") pattern. FIG. 17 illustrates the results for Sample 2 (laminate) and Sample 6 (stack), which each had a formed film layer with apertured protuberances in the 22 mesh hexagonal ("hex") pattern. FIG. 18 illustrates the results for Sample 3 (laminate) and Sample 7 (stack), which each had a formed film layer with apertured protuberances in the 40 mesh hexagonal ("hex") pattern. FIG. 19 illustrates the results for Sample 4 (laminate) and Sample 8 (stack), which each had a formed film layer with apertured protuberances in the 15 mesh blossom pattern.

Linear trendlines were generated for each set of data and included in the Figures. Table VI lists the slopes, intercepts, and $R^2$ values for the associated trendline for each sample.

TABLE VI

Summary of Linear Trendline Data from FIGS. 16-19

| Sample | Slope | Intercept | R2 |
|---|---|---|---|
| 1 | 23.27 | −4.04 | 0.96 |
| 2 | 21.81 | −3.85 | 0.96 |
| 3 | 21.53 | −4.14 | 0.90 |
| 4 | 17.42 | −3.72 | 1.00 |
| 5 | 41.16 | −8.03 | 0.99 |
| 6 | 24.02 | −5.01 | 0.98 |
| 7 | 26.45 | −5.71 | 0.99 |
| 8 | 27.19 | −4.95 | 0.98 |

FIGS. 16-19 and the linear trendlines indicate that for each of the apertured protuberance patterns, the laminates tend to have flatter slopes than the stacks, which provides an indication that the laminates do not compress as much as the stacks as the applied pressure is increased, especially for the 11 mesh hexagonal and 15 mesh blossom patterns. Without being bound by theory, it is postulated that for the laminates, the fibers of the nonwoven that are embedded in the lands of the apertured formed film provide a scaffolding structure that allows the apertured protuberances to better maintain their shape and not compress as much as apertured protuberances that do not have such a benefit. Such a benefit may provide a particular advantage so that the fluid distribution material performs well under the applied pressures experienced while being worn by a user.

Embodiments of the invention provide a fluid distribution material that reduces residual wetness, even after the absorbent article is subjected to pressure. The combination of the formed film layer, which has a lower basis weight compared to known film-only acquisition distribution materials, and the nonwoven layer laminated to the formed film layer may provide a modulus that is sufficient to allow the fluid distribution material to be converted into an absorbent article, as desired.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

For example, even though the testing was completed with the fluid distribution layer being oriented so that the insult contacted the formed film layer first, it is contemplated that in some embodiments, the fluid distribution layer may be used in an absorbent article with the nonwoven layer facing the topsheet and the formed film layer facing the absorbent core. The above-described and illustrated embodiments are not intended to be limiting in any way.

What is claimed is:

1. A fluid distribution material for use in an absorbent article, the fluid distribution material comprising:
   a formed film layer having a user-facing side and a garment-facing side opposite the user-facing side, the formed film layer comprising a plurality of apertured protuberances arranged in a pattern having 10 to 40 protuberances per linear inch, each of the protuberances comprising a continuous sidewall extending from the user-facing side, the garment-facing side having a plurality of apertures aligned with the plurality of apertured protuberances and land areas in between the apertures, the formed film layer having a basis weight of between about 10 gsm and about 25 gsm; and
   a nonwoven layer laminated to the garment-facing side of the formed film layer, the nonwoven layer comprising a plurality of fibers attached to the formed film layer at the land areas, the nonwoven layer having a basis weight of between about 10 gsm and about 15 gsm,
   wherein the fluid distribution material has a rewet value of less than 0.075 grams in accordance with the Rewet Test Method, and
   wherein the fluid distribution material has a compressibility of less than 10% between pressures of 0.21 psi and 0.60 psi.

2. The fluid distribution material according to claim 1, wherein the plurality of apertured protuberances are arranged in a pattern having 10 to 25 protuberances per inch.

3. The fluid distribution material according to claim 1, wherein the formed film layer comprises high density polyethylene (HDPE).

4. The fluid distribution material according to claim 1, wherein the formed film layer comprises a surfactant.

5. The fluid distribution material according to claim 1, wherein the nonwoven layer comprises a spunbond nonwoven.

6. The fluid distribution material according to claim 5, wherein the spunbond nonwoven 15 hydrophilic.

7. A fluid management system for use in an absorbent article, the fluid management system comprising:
   a fluid distribution material comprising
   a formed film layer having a user-facing side and a garment-facing side opposite the user-facing side, the formed film layer comprising a plurality of apertured protuberances arranged in a pattern having 10 to 40 protuberances per linear inch, each of the protuberances comprising a continuous sidewall extending from the user-facing side, the garment-facing side having a plurality of apertures aligned with the plurality of apertured protuberances and land areas in between the apertures, the formed film layer having a basis weight of between about 10 gsm and about 25 gsm, and
   a nonwoven layer laminated to the garment-facing side of the formed film layer, the nonwoven layer comprising a plurality of fibers attached to the formed film layer at the land areas, the nonwoven layer having a basis weight of between about 10 gsm and about 15 gsm; and
   a topsheet attached to the fluid distribution material, wherein the user-facing side of the formed film layer faces the topsheet,
   wherein the fluid distribution material has a rewet value of less than 0.075 grams in accordance with the Rewet Test Method, and
   wherein the fluid distribution material has a compressibility of less than 10% between pressures of 0.21 psi and 0.60 psi.

8. The fluid management system according to claim 7, wherein the plurality of apertured protuberances are arranged in a pattern having 10 to 25 protuberances per inch.

9. The fluid management system according to claim 7, wherein the formed film layer comprises high density polyethylene (HDPE).

10. The fluid management system according to claim 7, wherein the topsheet comprises an apertured formed film.

11. The fluid management system according to claim 7, wherein the topsheet comprises a nonwoven web.

12. The fluid management system according to claim 7, wherein the topsheet comprises a laminate.

13. An absorbent article comprising:
a topsheet;
a backsheet;
an absorbent material in between the topsheet and the backsheet; and
a fluid distribution material in between the topsheet and the absorbent core, the fluid distribution material comprising
a formed film layer having a user-facing side and a garment-facing side opposite the user-facing side, the formed film layer comprising a plurality of apertured protuberances arranged in a pattern having 10 to 40 protuberances per linear inch, each of the protuberances comprising a continuous sidewall extending from the user-facing side and contacting the topsheet, the garment-facing side having a plurality of apertures aligned with the plurality of apertured protuberances and land areas in between the apertures, the formed film layer having a basis weight of between about 10 gsm and about 25 gsm, and
a nonwoven layer laminated to the garment-facing side of the formed film layer, the nonwoven layer comprising a plurality of fibers attached to the formed film layer at the land areas, the nonwoven layer having a basis weight of between about 10 gsm and about 15 gsm,
wherein the fluid distribution material has a rewet value of less than 0.075 grams in accordance with the Rewet Test Method, and
wherein the fluid distribution material has a compressibility of less than 10% between pressures of 0.21 psi and 0.60 psi.

14. The absorbent article according to claim 13, wherein the plurality of apertured protuberances are arranged in a pattern having 10 to 25 protuberances per inch.

15. The absorbent article according to claim 13, wherein the formed film layer comprises high density polyethylene (HDPE).

16. The absorbent article according to claim 13, wherein the topsheet comprises an apertured formed film.

17. The absorbent article according to claim 13, wherein the topsheet comprises a nonwoven web.

18. The absorbent article according to claim 13, wherein the topsheet comprises a laminate.

* * * * *